US012303238B2

(12) United States Patent
Buller

(10) Patent No.: US 12,303,238 B2
(45) Date of Patent: May 20, 2025

(54) SYSTEM AND METHOD FOR DETERMINING AN ADAPTIVE PHYSIOLOGICAL STRAIN INDEX

(71) Applicant: The Government of the United States, as represented by the Secretary of the Army, Fort Detrick, MD (US)

(72) Inventor: Mark J Buller, Douglas, MA (US)

(73) Assignee: The Government of the United States, as represented by the Secretary of the Army, Ft. Detrick, MD (US)

( * ) Notice: Subject to any disclaimer, the term of this patent is extended or adjusted under 35 U.S.C. 154(b) by 0 days.

(21) Appl. No.: 18/100,361

(22) Filed: Jan. 23, 2023

(65) Prior Publication Data
US 2023/0148878 A1 May 18, 2023

Related U.S. Application Data

(63) Continuation of application No. 16/072,815, filed as application No. PCT/US2017/027985 on Apr. 17, 2017, now Pat. No. 11,564,579.
(Continued)

(51) Int. Cl.
*A61B 5/00* (2006.01)
*A61B 5/01* (2006.01)
(Continued)

(52) U.S. Cl.
CPC ............ *A61B 5/02055* (2013.01); *A61B 5/01* (2013.01); *A61B 5/11* (2013.01); *A61B 5/725* (2013.01);
(Continued)

(58) Field of Classification Search
None
See application file for complete search history.

(56) References Cited

U.S. PATENT DOCUMENTS 4,883,063 A * 11/1989 Bernard ............... A61B 5/6831
600/549
5,441,476 A 8/1995 Kitado et al.
(Continued)

FOREIGN PATENT DOCUMENTS

CA 2650576 A1 10/2006
FR 2998158 A1 5/2014
(Continued)

OTHER PUBLICATIONS

European Patent Office, extended European Search Report for EPO App. No. 17 783 371.2, Oct. 29, 2019.
(Continued)

*Primary Examiner* — Sana Sahand
(74) *Attorney, Agent, or Firm* — Leigh Z. Callander

(57) ABSTRACT

The invention in at least one embodiment includes a system and method for detecting and evaluating an adaptive physiological strain index (aPSI) of an individual with a processor and in a further embodiment taking into account the fitness, age and clothing of the individual based upon physiology. The invention in at least one embodiment includes a system and method to calculate the aPSI using physiological measures. In at least one embodiment, the method obtains an individual's skin temperature and heart rate in order to calculate the individual's aPSI.

20 Claims, 5 Drawing Sheets

Related U.S. Application Data

(60) Provisional application No. 62/323,268, filed on Apr. 15, 2016.

(51) Int. Cl.
*A61B 5/0205* (2006.01)
*A61B 5/11* (2006.01)

(52) U.S. Cl.
CPC .......... *A61B 5/441* (2013.01); *A61B 2503/20* (2013.01); *A61B 2562/0219* (2013.01)

(56) References Cited

U.S. PATENT DOCUMENTS

| | | | |
|---|---|---|---|
| 7,037,273 | B2 | 5/2006 | Zhu et al. |
| 7,171,251 | B2 | 1/2007 | Sarussi et al. |
| 7,251,454 | B2 | 7/2007 | White |
| 7,805,186 | B2 | 9/2010 | Pulkkinen et al. |
| 7,827,011 | B2 | 11/2010 | Devaul et al. |
| 7,883,463 | B2 | 2/2011 | Sattler et al. |
| 7,942,825 | B2 | 5/2011 | Ranganathan et al. |
| 8,204,786 | B2 | 6/2012 | Leboeuf et al. |
| 8,465,397 | B2 | 6/2013 | Saalasti et al. |
| 8,936,552 | B2 | 1/2015 | Kateraas et al. |
| 9,204,806 | B2 | 12/2015 | Stivoric et al. |
| 11,517,203 | B2 | 12/2022 | Reifman et al. |
| 11,540,723 | B2 | 1/2023 | Reifman et al. |
| 11,564,579 | B2 | 1/2023 | Buller |
| 2002/0009119 | A1 | 1/2002 | Matthew et al. |
| 2002/0165443 | A1 | 11/2002 | Mori |
| 2004/0034295 | A1 | 2/2004 | Salganicoff et al. |
| 2005/0113703 | A1 | 5/2005 | Farringdon et al. |
| 2007/0239038 | A1 | 10/2007 | Nicolaescu et al. |
| 2007/0295713 | A1 | 12/2007 | Carlton-Foss |
| 2008/0224866 | A1 | 9/2008 | Rehman |
| 2009/0069642 | A1 | 3/2009 | Gao et al. |
| 2009/0069647 | A1 | 3/2009 | McNames et al. |
| 2009/0198112 | A1* | 8/2009 | Park .............. A61B 5/02438 600/301 |
| 2010/0113894 | A1 | 5/2010 | Padiy |
| 2010/0280331 | A1 | 11/2010 | Kaufman et al. |
| 2011/0004072 | A1 | 1/2011 | Fletcher et al. |
| 2011/0144457 | A1 | 6/2011 | Coulon |
| 2011/0251495 | A1 | 10/2011 | Province et al. |
| 2011/0257542 | A1 | 10/2011 | Russell et al. |
| 2011/0288381 | A1 | 11/2011 | Bartholomew et al. |
| 2011/0301432 | A1 | 12/2011 | Riley et al. |
| 2012/0022336 | A1 | 1/2012 | Teixeira et al. |
| 2012/0068848 | A1 | 3/2012 | Campbell et al. |
| 2012/0078127 | A1 | 3/2012 | McDonald et al. |
| 2012/0197584 | A1 | 8/2012 | Coates |
| 2013/0237772 | A1 | 9/2013 | Pisani et al. |
| 2014/0180027 | A1 | 6/2014 | Buller |
| 2014/0249434 | A1 | 9/2014 | Banet et al. |
| 2014/0343372 | A1 | 11/2014 | Ahmed et al. |
| 2015/0031964 | A1 | 1/2015 | Bly et al. |
| 2015/0100135 | A1 | 4/2015 | Ives |
| 2015/0142332 | A1 | 5/2015 | Jeon et al. |
| 2015/0182130 | A1* | 7/2015 | Utter, II .............. A61B 5/0024 600/483 |
| 2016/0081629 | A1 | 3/2016 | Rostalski et al. |
| 2017/0071477 | A1 | 3/2017 | Lin et al. |
| 2017/0238811 | A1 | 8/2017 | Buller et al. |

FOREIGN PATENT DOCUMENTS

| | | |
|---|---|---|
| JP | 2005226902 A | 8/2005 |
| JP | 2018-134137 A | 8/2018 |
| WO | 2009034218 A | 3/2009 |
| WO | 2011032016 A1 | 3/2011 |
| WO | 2015185927 A1 | 12/2015 |
| WO | 2020/180454 A9 | 9/2020 |

OTHER PUBLICATIONS

Cuddy, John S. et al., "A reduced core to skin temperature gradient, not a critical core temperature, affects aerobic capacity in the heat," vol. 43, Jul. 2014, pp. 7-12.

Wright-Beatty, Heather E. et al., "Increased air velocity during exercise in the heat leads to equal reductions in hydration shifts and interleukin-6 with age," Jun. 19, 2014, vol. 114, Issue 10, pp. 2081-2092.

Esteve-Lanao, Jonathan, et al., "How Do Humans Control Physiological Strain during Strenuous Endurance Exercise?," PLoS One, vol. 3, No. 8, https://doi.org/10.1371/journal.pone.0002943, Aug. 13, 2008, pp. 1-11.

Pokora, Ilona, et al., "Application of A Physiological Strain Index in Evaluating Responses to Exercise Stress—A Comparison Between Endurance and High Intensity Intermittent Trained Athletes," Journal Human Kinetics, vol. 50, Apr. 13, 2016, pp. 103-114.

Wan, Margaret, "Assessment of Occupational Heat Strain," Scholar Commons, Graduate Theses and Dissertations, http://scholarcommons.usf.edu/etd/2745, Jul. 17, 2016, pp. 1-66.

Belval, Luke N., "Thermoregulatory Responses of Runners following a Warm-Weather Road Race," University Scholar Projects, https://opencommons.uconn.edu/usp_projects/7, Spring 2014, pp. 1-36.

Cuddy, John S., et al., "Skin Temperature and Heart Rate Can Be Used to Estimate Physiological Strain During Exercise in the Heat in a Cohort of Fit and Unfit Males," Military Medicine, vol. 178, Jul. 2013, pp. e841-e847.

Cuddy, John S., et al., "A reduced core to skin temperature gradient, not a critical core temperature, affects aerobic capacity in the heat," Journal of Thermal Biology, vol. 43, Apr. 18, 2014, pp. 7-12.

Ely, Brett R., "Evidence against a 40C core temperature threshold for fatigue in humans," Journal of Applied Physiology, vol. 107, Aug. 27, 2009, pp. 1519-1525.

Pandolf, Kent B., "Convergence of Skin and Rectal Temperatures as a Criterion for Heat Tolerance," Aviation, Space, and Environmental Medicine, vol. 49, Sep. 1978, pp. 1095-1101.

Varela, Manuel, et al., "Holter Monitoring of Central and Peripheral Temperature: Possible Uses and Feasibility Study in Outpatient Settings," Journal of Clinical Monitoring and Computing, Vo. 23, 2009, pp. 209-216.

Hunt, Andrew P., et al., "Indices of physiological strain for firefighters of the Australian Defence Forces," Journal of Occupational and Environmental Hygiene, https://doi.org/10.1080/15459624.2019.1666211, Oct. 11, 2019, pp. 1-8.

Deming, Nathan J., et al., "Letter to the Editor: In response to indices of physiological strain for firefighters of the Australian Defence Forces," Journal of Occupational and Environmental Hygiene, vol. 17, Nos. 7-8, https://doi.org/10.1080/15459624.2020.1772976, pp. D11-D12.

Deming, Nathan J., et al., "Letter to the Editor: Correspondence: Indices of physiological strain for firefighters of the Australian Defence Forces," Journal of Occupational and Environmental Hygiene, vol. 17, Nos. 7-8, https://doi.org/10.1080/15459624.2020.1772977, pp. D13-D14.

Davey, Sarah L., et al., "The physiological strain index does not reliably identify individuals at risk of reaching a thermal tolerance limit," European Journal of Applied Physiology, vol. 121, Mar. 2, 2021, pp. 1701-1713.

U.S. Patent and Trademark Office, Office Action in U.S. Appl. No. 16/327,846, filed Aug. 31, 2021, pp. 10-28.

Buller, Mark J., et al., "Real-Time Core Body Temperature Estimation from Heart Rate for First Responders Wearing Different Levels of Personal Protective Equipment," Ergonomics, http://dx.doi.org/10.1080/00140139.2015.1036792, 2015, pp. 1-12.

Gunga, H. C., et al., "The Double Sensor—A Non-Invasive Device to Continuously Monitor Core Temperature in Humans on Earth and in Space," Respiratory Physiology & Neurobiology, Oct. 2009, pp. S63-S68, vol. 169, Supplement.

Potter, Adam W., et al., "Mathematical Prediction of Core Body Temperature from Environment, Activity, and Clothing: The Heat Decision Aid (HSDA)," Journal of Thermal Biology, Jan. 16, 2017, pp. 78-85, vol. 64.

(56) References Cited

OTHER PUBLICATIONS

Richmond, Victoria L., et al., "Prediction of Core Body Temperature from Multiple Variables," Ann. Occup. Hyg., Aug. 12, 2015, pp. 1168-1178, vol. 59, No. 9.
Wilkerson, David M., et al., "The Effect of Cool Water Ingestion on Gastrointestinal Pill Temperature," Medicine & Science in Sports & Exercise, 2008, pp. 523-528, vol. 40, No. 3.
U.S Patent and Trademark Office, Office Action in U.S. Appl. No. 16/767,970, filed May 28, 2020, pp. 47-48.
Fiala, Dusan, et al., "Modeling in Physiology: A computer model of human thermo-regulation for a wide range of environmental conditions: the passive system," Journal of Applied Physiology, 1999, pp. 1957-1972, vol. 87, No. 5.
Gribok, Andrei, et al., "Regulation of Body Core Temperature Prediction during Physical Activity," Proceedings of the 28th IEEE EMBS Annual International Conference, Aug. 30-Sep. 3, 2006, pp. 459-463.
Laxminarayan, Srinivas, et al., "Preventing heat injuries by predicting individualized human core temperature," 2015, STO-MP-HFM-254, pp. 1-11.
Montain, Scott, J., et al., "Physiological tolerance to uncompensable heat stress: effects of exercise intensity, protective clothing, and climate," Journal of Applied Physiology, 1994, pp. 216-222, vol. 77, No. 1.
Oleng, Nicholas, O., et al., "Hybrid Approaches to Physiologic Modeling and Prediction," Biomonitoring for Physiological and Cognitive Performance during Military Operations, Proceedings of SPIE, 2005, pp. 193-203, vol. 5797.
Sawka, Michael, et al., "Integrates Physiological Mechanisms of Exercise Performance, Adaptation, and Maladaptation to Heat Stress," Comprehensive Physiology, Oct. 2011, pp. 1883-1928, vol. 1.
Al-Mukhaizeem, F. et al.: "Comparison of temporal artery, rectal and esophageal core temperature in children: results of pilot study", Pediatric Child Health, Sep. 2004, pp. 461-465, vol. 9.
Bland, J. and Altman, D.: "Statistical methods for assessing agreement between two methods of clinical measurements," Lancet, 1986, pp. 307-310, vol. 1.
Braur, A., et al: "Determination of core body temperature. A comparison of esophogeal, bladder and rectal temperature: A comparison of esophageal, bladder and rectal temperature during post-operative rewarming" (translated title), Der Anaesthesist, Fall 1997, pp. 683-688, vol. 46.
Buller, MJ. et al., "Thermal work strain during Marine rifle squad operations in Afghanistan (Mar. 2010)," USARIEM Technical Report No. T11-02 (Ad A501301), Mar. 2010, pp. 1-39.
Buller, Mark J, et al. "Estimation of Human Internal Temperature from Wearable Physiological Sensors." IAAI. 2010.
Buller, M.J. et al.; "Human thermoregulatory system state estimation using non-invasive physiological sensors," in Engineering in Medicine and Biology Society, EMBC, 2011 Annual International Conference of the IEEE, vol., No., pp. 3290-3293, Aug. 30, 2011-Sep. 3, 2011.
Buller, M.J. et al., "Estimation of human core temperature from sequential heart rate observations," Physiological Measurement, 2013, pp. 781-798, vol. 34.
Byrne, C. and Lim, C.L., "The ingestible telemetric body core temperature sensor: a review of validity and exercise applications," Br. J. Sport Med., 2007, pp. 126-133, vol. 41.
Cheuvront, Samuel et al., "Evaluation of the limits to accurate sweat loss prediction during prolonged exercise," Eur. J. Appl. Physiol., 2007, pp. 215-224, vol. 101.
Cuddy, JS et al., abstract for "Skin temperature and heart rate can be used to estimate physiological strain during exercise in the heart in a cohort of fit and unfit males," Association of Military Surgeons of the U.S., Mil Med., Jul. 2013.
Degroot, David W. et al., "Prediction Models for Core Temperature During Heat Stress Vary with Exercise Intensity," Medicine & Science in Sports & Exercise, May 2007, p. S436, vol. 39, issue 5.
Degroot, David W. et al., "Validation of the ICDA model for predicting body core temperature," Medical & Science in Sports & Exercise, May 2008, p. S367, vol. 40, issue S.
Fiala, Dusan et al., "Computer prediction of human thermoregulatory and temperature responses to a wide range of environmental conditions," International Journal Biometeorol, 2001, pp. 143-159, vol. 45.
Fick, Adolph, "On liquid diffusions," Journal of Membrane Science, 1995, pp. 30-39, vol. 10.
Fox, R.H. et al., "A new method for monitoring deep body temperature from the skin surface," Clinical Science, 1973, pp. 81-86, vol. 44.
Frank, A. et al., "The cumulative heat strain index—a novel approach to assess the physiological strain induced by exercise heat stress," Eur. J. Appl. Physiol., 2001, pp. 527-532, vol. 84.
Grubbs, Frank E., "Procedures for detecting outlying observations in samples," AD-781 499, BRL Report No. 1713, Apr. 1974, pp. 1-53.
Gunga, Hanns-Christian et al., "A non-invasive device to continuously determine heat strain in humans," Journal of Thermal Biology, 2008, pp. 297-307, vol. 33.
Gunga, H.C., et al., "The double sensor—a non invasive device to continuously monitor core temperature in humans on earth and in space," Respir. Physiol, Neurobiology, 2009, pp. S63-S68, vol. 169S.
Havenith, George, "Individualized model of human thermoregulation for the simulation of heat stress response," J. Appl. Physiol., 2001, pp. 1943-1954, vol. 90.
Sargent II, Frederick et al., "Physiological variability in young men," Physiological Measurements of Metabolic Functions, ed. CF Consolazio, RE Johnson and LJ Pecora, 1963, pp. 453-480, New York: McGraw-Hill.
Kalman, R.E., "A New Approach to Linear Filtering and Prediction Problems," Journal of Basic Engineering, Mar. 1960, pp. 35-45, vol. 82.
Karp, Jason R., "Heart Rate Training for Improved Running Performance," www.coachr.org/heart_rate_training_for_improvement.htm., printed on Mar. 29, 2016.
Kenefick, Robert W. et al., "DEET insect repellent: effects on thermoregulatory sweating and physiological strain," Eur. J. Appl. Physiol., 2011, pp. 3061-3068, vol. 111.
Kraning, Kenneth K., "A mechanistic computer simulation of human work in heat that account for physical and physiological effects of clothing, aerobic fitness and progressive dehydration," Journal of Thermal Biology, 1997, pp. 331-342, vol. 22, No. 415.
Latzka, William A. et al., "Hyperhydration: thermoregualtory effects during compensable exercise heat stress," J. Appl. Physiol., 1997, pp. 860-866, vol. 83.
Latzka, William A. et al., "Hyperhydration: tolerance and cardiovascular effects during uncompensible exercise heat stress," J. Appl. Physiol., 1998, pp. 1858-1864, vol. 84.
Lee, Jason K.W. et al., "Thermoregulation, pacing and fluid balance during mass participation distance running in a warm and humid environment," Eur. Jour. Appl. Physiol., 2010, pp. 887-898, vol. 109.
Lefrant, J.Y. et al., "Temperature measurement in intensive care patients: comparison of urinary bladder, besophageal, rectal, axillary, and inguinal methods versus pulmonary artery core method," Intensive Care Med., 2003, pp. 414-418, vol. 29.
Lim, Chin Leong et al., "Human Thermoregulation and Measurement of Body Temperature in Exercise and Clinical Settings," Annals Academy of Medicine, Apr. 2008, pp. 47-53, vol. 37, Singapore.
Montain, Scott J. et al., "Influence of graded dehydration on hyperthermia and cardiovascular drift during exercise," J. Appl. Physiol., 1992, pp. 1340-1350, vol. 73.
Moran, Daniel S. et al., "A physiological strain index to evaluate heat stress," American Journal of Physiological Regulation Integr. Comp. Physiol., 1998, pp. R129-R134, vol. 275.
Niedermann, Reto et al., "Prediction of human core body temperature using non-invasive measurement methods," International Journal of Biometeorology, published online Jun. 13, 2013, pp. 1-9.

(56) References Cited

OTHER PUBLICATIONS

Orderud, Fredrik, "Comparison of Kalman Filter Estimation Approaches for State Space Models with Nonlinear Measurements," In. Proc. of Scandinavian Conference on Simulation and Modeling, pp. 1-8, 2005.

Sawka, Michael N. et al., "Chapter 26 Physiological Systems and Their Responses to Conditions of Heat and Cold," ACSM's Advanced Exercise Physiology, ed. CM Tipton, MN Sawka, CA Tate, and RL Terjung, pp. 535-563, Williams & Wilkins, New York.

Steck, Luke N. et al., "Non-invasive measurement of the human core temperature," International Journal of Heat and Mass Transfer, 2011, pp. 975-982, vol. 54.

Welch, Greg et al., "An introduction to the Kalman Filter," Technical Report TR 95-041, Department of Computer Science, 2001, pp. 19-29, University of North Carolina at Chapel Hill, NC.

Yokota, Miyo et al., "Thermoregulatory model to predict physiological status from ambient environment and heart rate," Computers in Biology Medicine and Medicine, 2008, pp. 1187-1193, vol. 38.

Espacenet, English abstract for FR2998158 A1, printed on Mar. 21, 2016.

Espacenet, English abstract for JP2005226902 A, printed on Mar. 21, 2016.

U.S. Patent and Trademark Office, Office Action in U.S. Appl. No. 14/107,920, filed Sep. 25, 2015.

U.S. Patent and Trademark Office, Final Office Action in U.S. Appl. No. 14/107,920, filed May 4, 2016.

U.S. Patent and Trademark Office, International Search Report and Written Opinion for PCT App. No. PCT/US2017/027985, Jun. 29, 2017.

Teunissen, LPJ et al., "Non-invasive continuous core temperature measurement by zero heat flux," Physiological Measurement, 2011, pp. 559-570, vol. 32.

Yamakage, Michiaki et al., "Evaluation of newly developed monitor of deep body temperature," Journal of Anesthesia, 2002, pp. 354-357, vol. 16.

Ozaki, T., et al., "The local linearization filter with application to nonlinear system identifications," Proc. first US/Japan Conf Frontiers Stat Modeling: An Information Approach, Springer, pp. 217-240, 1994.

Chen, Chi-Tsong, "Linear System Theory and Design," 3rd ed. Oxford, NY: Oxford University Press, 1999, pp. 106-111.

Bulut, Yalcin, et al., "Process and Measurement Noise Estimation for Kalman Filtering," Structural Dynamics, Conf Proc Soc Exp Mech Series 3, pp. 375-386, 2011.

Basler, Jeremy Curtis, "The Ability of a Novel Physiological Strain Scale to Predict Heat Strain Risk in Field Settings Using Non-Invasive Measures of Heart Rate and Skin Temperature," Graduate Student Theses, Dissertations, & Professional Papers, 10626, https://scholarworks.umt.edu/etd/10626, 2013, pp. 1-44.

Buller, Mark J., et al., "A real-time heat strain risk classifier using heart rate and skin temperature," Physiological Measurement, 2008, vo. 29, N79-N85.

European Patent Office, English abstract for JP2018134137A, printed on Apr. 28, 2023.

\* cited by examiner

SYSTEM AND METHOD FOR DETERMINING AN ADAPTIVE PHYSIOLOGICAL STRAIN INDEX

This patent application is a continuation application from U.S. patent application Ser. No. 16/072,815, filed on Jul. 25, 2018, which is a 371 National Stage application from International Application No. PCT/US2017/027985, filed on Apr. 17, 2017, which claims priority to and the benefit of U.S. Patent Application No. 62/323,268 filed on Apr. 15, 2016, both of which are hereby incorporated by reference.

I. FIELD OF THE INVENTION

This invention in at least one embodiment relates to determining an adaptive physiological strain index (aPSI) using a body core temperature, a skin temperature, and a heart rate of an individual.

II. BACKGROUND OF THE INVENTION

Hot environments pose a risk of heat illness to people in occupations where heavy workloads and/or protective clothing ensembles are necessary. Excessive heat strain can lead to collapse or even death. Heat-related illness (HRI) has a spectrum of disorders due to environmental heat exposure and includes minor conditions such as heat cramps, heat syncope, and heat exhaustion as well as the more severe condition known as heat stroke.

HRI is an ever present threat to athletes, military personnel, and occupational hazard workers, as the combination of physical exertion in hot environments makes individuals susceptible to heat stroke, heat exhaustion, and heat cramps. HRI prevention includes avoiding medications that can increase the risk of heat illness (e.g., antihypertensives, diuretics, and anticholinergics), gradual adjustment to heat, and sufficient fluids and electrolytes. Mild HRI can be treated by drinking fluids. In more significant HRI cases, spraying with mist and using a fan is useful. For those with severe HRI putting them in lukewarm to cold water is recommended if possible with transport to a hospital.

Efforts to identify and control the incidence of heat illness/injury originally focused on identifying high risk environments and modifying work/rest schedules. Although the risk of heat illness can be reduced by acclimation, appropriate work rest schedules, and proper hydration, the risk is never entirely abated when there is heavy exertion in a hot environment.

Assessing risk of heat stress from environmental conditions alone fails to account for individual differences, such as acclimation status, fitness, body composition and morphology, prior heat injury, (which can play a role in an individual's response to working in hot environments) and clothing.

Personal physiological monitoring is one means of overcoming the limitations of assessing heat strain using environment monitoring alone. Modern physiological monitoring systems are becoming more common for monitoring applications; however, while a number of physiological strain indices can be computed from a number of different physiological variables none to date take account of the interplay between an individual's age, fitness, and personal protective equipment being worn.

III. SUMMARY OF THE INVENTION

By combining physiological measures into a single adaptive index of physiological strain (aPSI) it is possible to provide an assessment of risk of HRI to an individual being monitored.

In at least one embodiment, a system for generating an adaptive physiological strain index (aPSI) where the system includes: at least one heart rate sensor configured to be attached to or placed on a person; at least one temperature sensor configured to detect a skin temperature of the person; and a processer configured to produce an aPSI score for the person using a temperature gradient between the skin temperature from the at least one temperature sensor and a body core temperature determined based on the heart rate from the at least one heart rate sensor.

In at least one embodiment, a system for detecting aPSI for a person (or individual) where the system includes: a heart rate means for detecting a heart rate of a person; a temperature means for detecting a skin temperature of the person; an input means for receiving a person's age; a calculation means for producing an aPSI score for the person based on the detected skin temperature, the detected heart rate, the received input age, and temperature gradient between the detected skin temperature and a body core temperature calculated based on the detected heart rate; and storage means for storing heart rates from the heart rate means, skin temperatures from the temperature means, and body core temperatures from the calculation means.

In at least one embodiment, a system includes: at least one temperature sensor configured to be attached to an individual's skin; at least one heart rate sensor configured to be attached to the individual; a memory for storing at least a resting heart rate for the individual; a processor in electrical communication with the at least one temperature sensor and the at least one heart rate monitor, the processor configured to produce aPSI score for the individual based on the current skin temperature, the resting heart rate, and the current heart rate where the body core temperature is calculated based on the heart rate information and time since initiation of the monitoring, or the body core temperature is obtained from an internal temperature sensor in the individual.

In at least one embodiment, a system includes: at least one skin temperature sensor configured to be attached to an individual's skin; at least one heart rate sensor configured to be attached to the individual; at least one internal temperature sensor configured to be internal to the individual's skin; a memory for storing at least a resting heart rate for the individual; a processor in electrical communication with the at least one temperature sensor and the at least one heart rate monitor, the processor configured to produce aPSI score for the individual based on the current skin temperature from the at least one skin temperature sensor, the resting heart rate from the memory, the current heart rate from the at least one heart rate sensor, and the body core temperature from the internal temperature sensor.

Further to any of the above embodiments, the system further includes a data storage configured to store data related to an age of the person; and where the processor calculating the aPSI score based on the following equation:

$$aPSI = 5\left(\frac{CT_t - CT_{rest}}{CT_{critical} - CT_{rest}}\right) + 5\left(\frac{HR_t - HR_{rest}}{HR_{critical} - HR_{rest}}\right)$$

$$HR_{critical} = 0.90\ (220 - age)$$

$$CT_{critical} = 39.5°\ C. + \frac{(CT_t - ST_t) - 4}{4}$$

where $CT_t$ is the body core temperature at a time t, $CT_{rest}$ is the body core temperature at rest, $HR_t$ is the heart rate at a time t, $HR_{rest}$ is the heart rate at rest, $HR_{critical}$ is a maximum heart rate, $CT_{critical}$ is a maximum body temperature, and ST is the skin temperature. Further to the previous embodiment, the processor adjusts the aPSI score based on at least one of a fitness level, an age, a maximum heart rate, and a resting heart rate of an individual. Further to the previous two embodiments, wherein the aPSI score is recalculated at predetermined intervals when a variance is detected in at least one of the detected skin temperature and the detected heart rate. Further to the previous three embodiments, the equation uses an individual specific heart rate critical for the individual while using the following equations:

$$aPSI = 5\left(\frac{CT_t - CT_{rest}}{CT_{critical} - CT_{rest}}\right) + 5\left(\frac{HR_t - HR_{rest}}{HR_{critical} - HR_{rest}}\right)$$

$$CT_{critical} = 39.5° \text{ C.} + \frac{(CT_t - ST_t) - 4}{4}$$

Further to any of the above embodiments, where the processor configured to produce a new calculated aPSI score at predetermined intervals based on variances in at least one of the skin temperature and the heart rate received by the processor. Further to any of the above embodiments, the system further including a timer circuit in communication with the processor, and where the processor configured to produce a new calculated aPSI score based on calculating at least one first aPSI score at an initial time designation of a timer circuit and calculating a new aPSI score at predetermined time intervals as provided by the timer circuit. Further to the previous embodiment, the system further includes an accelerometer in communication with the processor; and where the processor is configured to detect at least one of a resting heart rate and a resting skin temperature of the individual when a plurality of signals from the accelerometer remained below a predetermined threshold for a predetermined time period and/or substantially remained below the predetermined threshold for the predetermined time period, and the processor further configured to determine a resting body core temperature for the individual based on the resting heart rate.

Further to any of the above embodiments, where the processor calculates the body core temperature using a Kalman filter or an extended Kalman filter. Further to any of the above embodiments, the system including a display in communication with the processor to display the calculated aPSI index produced by the processor. Further to any of the above embodiments, the system including an alarm in communication with the processor. Further to the previous embodiment, the processor is configured to produce an alert signal to the alarm when the calculated aPSI score exceeds a predetermined aPSI score threshold. Further to any of the above embodiments, the system is housed in a wearable device.

In at least one embodiment, a method for generating an adaptive physiological strain index (aPSI) from a body temperature and heart rate for an individual, the method includes: receiving by a processor a heart rate signal from a heart rate sensor detecting a heart rate of the individual; receiving by the processor a skin temperature reading from a temperature sensor detecting a skin temperature of the individual; calculating with the processor a body core temperature for the individual based on the heart rate signal; calculating with the processor a temperature gradient between the skin temperature reading and the body core temperature; calculating with the processor an aPSI score for the individual using the body core temperature, the temperature gradient and the heart rate signal; and producing the calculated aPSI score from the processor.

In at least one embodiment, a method for generating an adaptive physiological strain index (aPSI) from a skin temperature, a body core temperature and a heart rate, the method includes: receiving by a processor a heart rate signal from a heart rate sensor; receiving by the processor a skin temperature reading from a skin temperature sensor; receiving by the processor a body core temperature from an internal temperature sensor; calculating with the processor a temperature gradient between the skin temperature reading and the body core temperature reading; calculating with the processor an aPSI score for the person using the body core temperature, the temperature gradient and the heart rate signal; and producing the calculated aPSI score from the processor, and when one of the physiological readings is unavailable, using a previously stored value or calculating a value for the physiological reading.

According to either of the above method embodiments, the method further includes receiving the individual's age from at least one of an input device, memory, database, or data storage, wherein the person's age data can be accessed by the processor. Further to the previous embodiment, where calculating the aPSI score is based on said processor calculating the aPSI score based on the following equation:

$$aPSI = 5\left(\frac{CT_t - CT_{rest}}{CT_{critical} - CT_{rest}}\right) + 5\left(\frac{HR_t - HR_{rest}}{HR_{critical} - HR_{rest}}\right)$$

$$HR_{critical} = 0.90 \ (220 - \text{age})$$

$$CT_{critical} = 39.5° \text{ C.} + \frac{(CT_t - ST_t) - 4}{4}$$

where $CT_t$ is a body core temperature at a time t, $CT_{rest}$ is a body core temperature at rest, $HR_t$ is the heart rate at a time t, $HR_{rest}$ is a heart rate at rest, $HR_{critical}$ is a maximum heart rate, and $CT_{critical}$ is a maximum body temperature.

According to any of the above method embodiments, the method further includes calculating by the processor the body core temperature based on a Kalman filter or an extended Kalman filter. According to any of the above method embodiments, the method further includes when the received body temperature exceeds a predetermined threshold, generating an alert signal by the processor for an alarm. According to any of the above method embodiments, the method further includes adjusting by the processor the aPSI score based on at least one of a fitness level, an age, a maximum heart rate, or a resting heart rate of the individual. According to any of the above method embodiments, the method further includes said processor configured to produce a new calculated aPSI score at predetermined intervals based on at least one of variances in the detected body temperature by the temperature sensor and the detected heart rate by the heart rate sensor. According to any of the above method embodiments, the method further includes calculating with the processor new calculated aPSI scores at predetermined time intervals.

IV. BRIEF DESCRIPTION OF THE DRAWINGS

V. DETAILED DESCRIPTION OF THE DRAWINGS

The invention in at least one embodiment includes a system and a method to calculate an index of heat strain (e.g., 0=no strain, 9=very high strain) using physiological measures. Prior indices did not include an ability for application to different populations, different work, and/or protective clothing environments. Table 1 shows the original PSI levels and the associated levels of thermal work strain according to Moran et al. (1998):

TABLE 1

| PSI | Strain |
|---|---|
| 0 | |
| 1 | No/Little |
| 2 | |
| 3 | Low |
| 4 | |
| 5 | Moderate |
| 6 | |
| 7 | High |
| 8 | |
| 9 | Very High |
| 10 | |

It has been found in the past that it is possible to exceed a PSI of 10 under certain circumstances. The above table is relevant for at least one of the disclosed embodiments, the adaptive physiological strain index ("aPSI" or "adaptive PSI") provides a strain index score between 0 and 10 that takes into account the conditioning of the individual, the environment they are in, and the clothing they are wearing while being monitored. Existing systems would have a marathon runner having a high PSI (e.g., 11 or 12) compared to an individual wearing a fully enclosed Hazmat suit having a lower PSI (e.g., 7.5). An observer would deem the Hazmat suit individual being under more strain than the marathon runner. In at least one embodiment, this invention addresses this inaccuracy.

In at least one embodiment, a system and/or a method is provided to use an individual's body core temperature in connection with their heart rate and skin temperature to determine their aPSI. The invention in at least one embodiment includes a method for detecting and evaluating the aPSI of the individual with a processor having suitable programming to perform the functions discussed in this disclosure. In at least one embodiment, the relationship between the body core temperature and heart rate is a quadratic relationship that varies over a range of heart rate measurements, where in at least one embodiment the range is between 50 and 180 beats/minute, and in a further embodiment, the maximum heart rate is set to 220 minus the person's age with a corresponding quadratic relationship. In a further embodiment, the system and method use a Kalman filter model or an extended Kalman filter to determine the body core temperature. In at least one embodiment, the system and method calculate and adjust for external factors that may influence the adaptive physiological strain index, such as the environment, clothing, physical fitness, and the person's age or weight.

Figure 1:
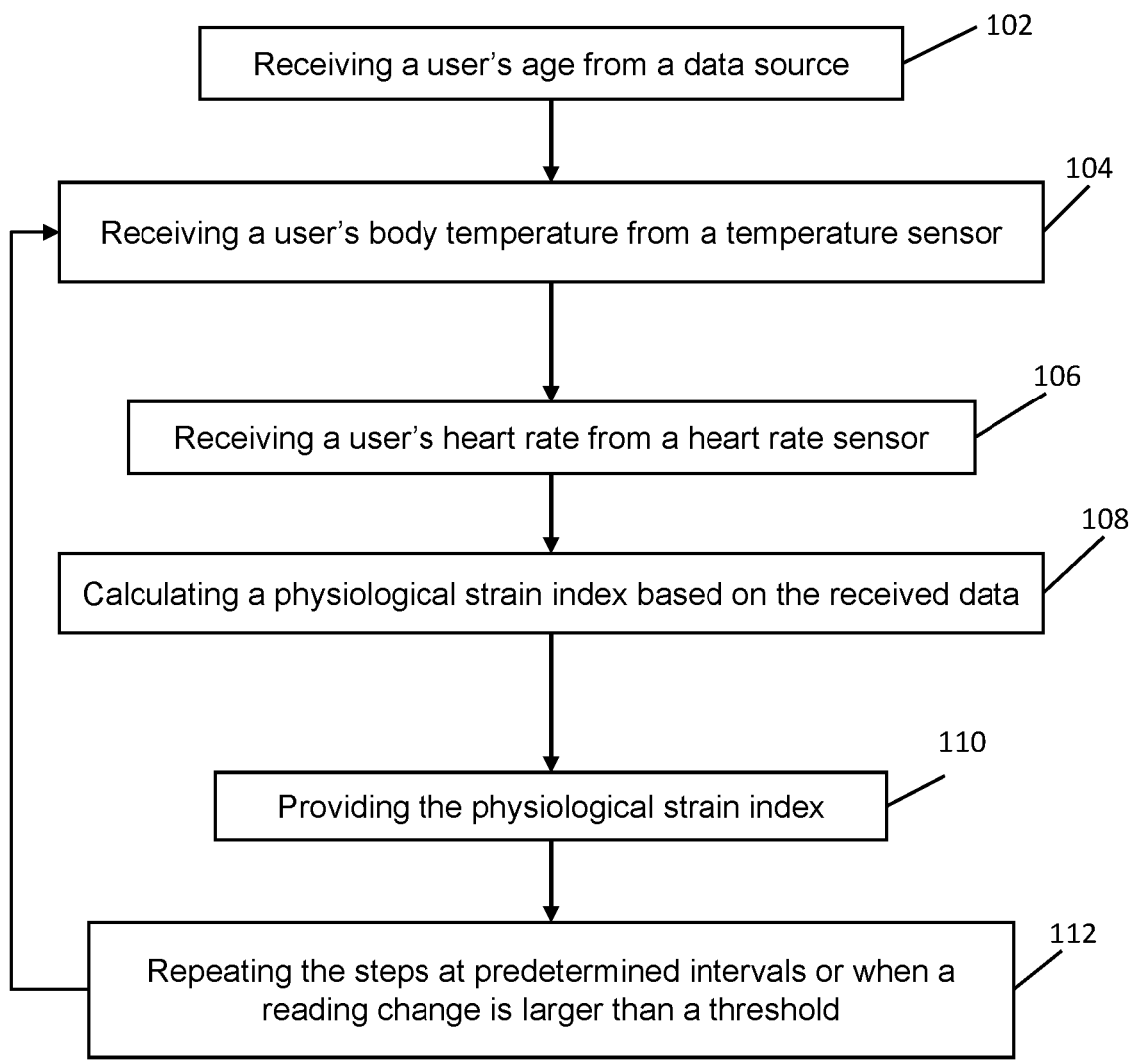
FIG. 1 illustrates a method according to one embodiment of the system.

FIG. 1 illustrates a method for operation of at least one system embodiment like those illustrated in FIGS. 2-6. A processor 210 receives the individual's age from a data source, 102. Examples of how the individual's age can be received include: 1) the individual providing his/her age is received through an input device such as a keyboard or other data entry mechanism including virtual versions; 2) retrieval of stored data about the individual; and 3) a combination of the previous two examples. In an alternative embodiment, this step is omitted from the method. In an alternate embodiment, the resting physiological information is provided in a similar manner at least as a starting point.

The processor 210 receives a skin temperature from at least one temperature sensor 230, 104. The processor 210 receives a measured heart rate from a heart rate sensor 220, 106. In at least one embodiment, there is one component that provides the skin temperature and the individual's heart rate. In at least one alternative embodiment, the processor sends a request for the person's skin temperature and/or heart rate to the appropriate sensor(s) for a reading instead of a continual data feed from these sensors.

In at least one embodiment, steps 102 through 106 can be performed in a different order and/or substantially simultaneous or substantially concurrently with each other.

The processor 210 calculates the aPSI score for the individual, 108. In at least one embodiment, the aPSI score is determined based on a quadratic calculation of the values of at least one of received skin temperature, the received heart rate, and the received age of the individual. In at least one embodiment, the aPSI score is calculated using a critical body core temperature that is based on a temperature gradient between the resting body core temperature, which is calculated based on the heart rate in at least one embodiment, and the skin temperature.

In at least one embodiment, the body core temperature is calculated in a multi-step process using an extended Kalman filter as discussed in U.S. Pat. App. Pub. No. US-2014-0180027-A1, which is hereby incorporated by reference. In a further embodiment, the processor can produce the body core temperature for the individual using a number of factors for an individual based on physical characteristics such as height, weight, and age. In at least one embodiment, using any known way to estimate a body core temperature including using any combination of skin temperature, physiological data, accelerometer data, environmental information, and clothing information.

The processor then provides the calculated aPSI score, 110. The calculated aPSI score may be provided to a display, a memory, a transmission system for relaying to an external device or system, and an alarm. The aPSI provides an improved indication of the current physiological strain of the individual being monitored, and would allow for an activity or pace change by the individual, if possible, to lower the physiological strain.

Repeating the receiving (104 and 106), calculating (108) and providing (110) steps at predetermined intervals, 112. Examples of predetermined intervals include 30 second intervals, 1 minute intervals, 2 minute intervals, 5 minute intervals, and 10 minute intervals, and hour intervals. In a further embodiment, the method includes setting or selecting the predetermined interval prior to calculating the aPSI score. In at least one further embodiment, a timer (or timer circuit or timing circuit) 340 illustrated in FIG. 3 can be used to delay the repeat cycle after calculating each aPSI score. In at least one embodiment, the aPSI score is calculated at variable times based on a change in the detected temperature, the heart rate that exceeds a predetermined threshold, the rate of change at least one physiological signal (e.g., skin temperature or heart rate) over a predetermined change time, or a combination of these.

Figure 4:
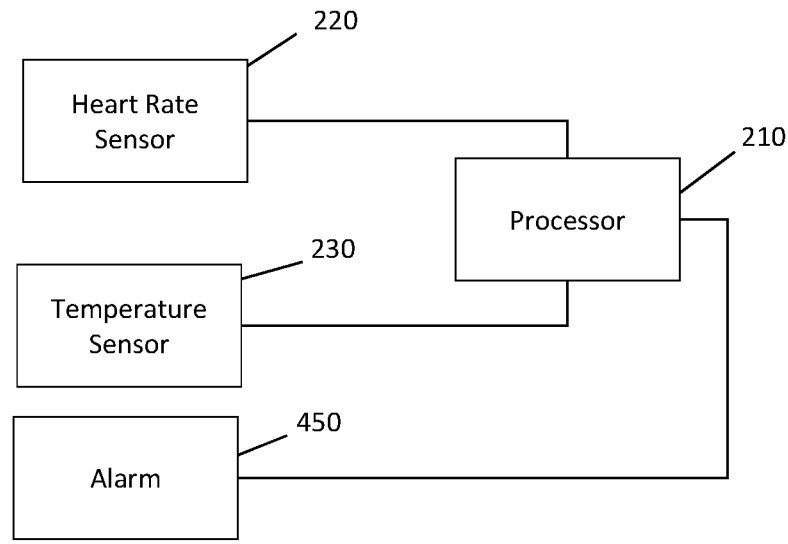
FIG. 4 illustrates a system according to at least one embodiment of the invention.

In at least one further embodiment, when the aPSI score exceeds a predetermined alarm threshold, an alert is generated by an alarm 450 of FIG. 4. In at least one embodiment, the processor 210 provides an alarm signal to the alarm 450 that triggers the alert.

Figure 5:
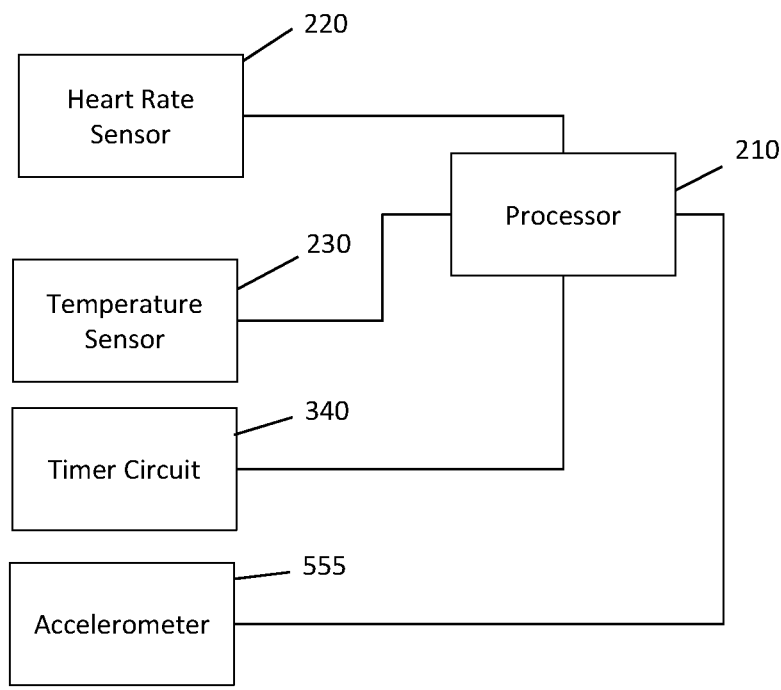
FIG. 5 illustrates a system according to at least one embodiment of the invention.

In a further embodiment illustrated in FIG. 5, the system includes at least one accelerometer 555 to monitor activity of the individual to facilitate obtaining resting physiological information about the individual such as resting body core temperature ($CT_{rest}$) and resting heart rate ($HR_{rest}$) and in other embodiments, the skin temperature. The illustrated system also includes the timer circuit 340. The processor 210 is in electrical communication with the timer circuit 340 and the accelerometer 555 to detect when the accelerometer 555 signal(s) are below a predetermined threshold for a predetermined time based on a time signal from the timer circuit 340.

In at least one embodiment, when the accelerometer signal(s) decreases below the predetermined threshold, the processor 210 stores the current time data in memory for later comparison or alternatively begins a counter that is incremented based on the time signal. Under the comparison embodiment, when the current time data is greater than the stored time data by the predetermined time, the processor 210 pulls and/or processes the signal from the heart rate sensor 220 to obtain the resting heart rate, which then is used to determine the resting body core temperature. Under the counter embodiment, the processor 210 increments the counter based on the time signal until it matches and/or exceeds the predetermined time before pulling and/or processing the signal from the heart rate sensor 220.

In a further embodiment, when the accelerometer signal (s) exceeds the predetermined threshold momentarily before decreasing below, the time does not reset. In such a situation, the accelerometer signal(s) has substantially remained below the predetermined threshold.

In at least one embodiment, the predetermined time is 20 minutes, 25 minutes, 30 minutes, 35 minutes, etc. In an alternative embodiment, the predetermined time is shorter such as 10 minutes or 15 minutes, and the processor 210 compares the heart rate signal starting at the predetermined time to follow-on recordings while the accelerometer signal (s) remains below the predetermined threshold to determine whether the heart rate signal has stabilized. Stabilized as used in this disclosure means that the signal level falls within a range set in the processor 210 for the physiological characteristic being monitored.

Using any of the previously mentioned variables, the modified and adaptive PSI includes an ability for application to different populations, different work, diverse age ranges, and/or protective clothing environments. The equation for the adaptive PSI score in at least one embodiment is as follows:

$$aPSI = 5\left(\frac{CT_t - CT_{rest}}{CT_{critical} - CT_{rest}}\right) + 5\left(\frac{HR_t - HR_{rest}}{HR_{critical} - HR_{rest}}\right)$$

$$HR_{critical} = 0.90\ (220 - age)$$

-continued
$$CT_{critical} = 39.5 + \frac{(CT_t - ST_t) - 4}{4}$$

In the adaptive PSI equation, the $CT_t$ is the body core temperature at a time t, $CT_{rest}$ is the body core temperature at rest, $HR_t$ is heart rate at a time t, and the $HR_{rest}$ is heart rate at rest, the $HR_{critical}$ is a critical maximal heart rate threshold used to determine a maximal aPSI. In at least one embodiment the $HR_{critical}$ in the adaptive PSI equation has a value as 90% of $HR_{max}$ as suggested by the American College of Sports Medicine Guidelines (America College 1991) and also includes the variable (220-age) for the $HR_{critical}$ value to be configured to apply to individuals of any age. In an alternate embodiment, the $HR_{critical}$ can be set as 90% of $HR_{max}$ derived from a $VO_2$ max test. In at least one embodiment, the $HR_{critical}$ is determined for the particular person based on previous physiological measurements.

The adaptive PSI equation also includes $CT_{critical}$ as the critical body core temperature which is adapted in real-time based on a body core temperature ($CT_t$), a skin temperature ($ST_t$), and a critical temperature such as 39.5° C. During activity the $CT_{critical}$ will vary based on a temperature gradient between the current core temperature and the current skin temperature.

In at least one embodiment, the method and system are able to adapt to constraints on available physiological data for use.

In the case of resting body core temperature and resting heart rate, the values used may be preset, entered by the individual or another person as discussed previously, or based on physiological measurements taken at rest. When the resting body core temperature is not available, then it may be set to 37.1° C. or calculated from the resting heart rate using, for example, a Kalman filter or an extended Kalman filter or other similar estimation for body core temperature based on heart rate. When the resting heart rate is not available, then it may be set at 71 beats per minute. In at least one embodiment, the system is prompted to take the current heart rate by a user or the individual to establish the individual's resting heart rate.

In at least one embodiment, the critical heart rate ($HR_{critical}$) is set to 180 beats per minute. In other embodiments, it is set based on the individual's age using the equation above or is obtained from another source for this specific individual based on physiological testing.

When the skin temperature is unavailable, the skin temperature is set to body core temperature minus four degrees Celsius in at least one embodiment. In at least one further embodiment, the critical body core temperature ($CT_{critical}$) is set based on the clothing being worn by the individual. In a further embodiment, $CT_{critical}$ is set as follows:

TABLE 2

| $CT_{critical}$ Values based on Clothing | |
|---|---|
| Full Encapsulation in PPE | about 38.5° C. or less |
| Long Sleeves and Pants | about 39.5° C. or less |
| Shorts and T-shirt | about 40.0° C. |
| Default Setting | 39.5° C. |

As discussed above, $CT_{critical}$ may be set pursuant to the equation above when the resting body core temperature and the skin temperature are known. In a further embodiment, the skin temperature is modified based on the location of the sensor used to obtain the skin temperature to take into account the gradient that is present on an individual's skin based on body location.

In other embodiments, where just the heart rate is available for the individual (for example, if the skin temperature sensor is omitted or not providing data), the body core temperature is calculated from the heart rate and $CT_{critical}$ is set to 39.5° C. When heart rate and skin temperature are available for the individual, using the equations above and calculating body core temperature from the heart rate. When the embodiment also includes a sensor for body core temperature, then using heart rate and body core temperature to determine the aPSI and taking into account whether skin temperature is available or not and adjusting accordingly using the above-described approaches.

Figure 2:
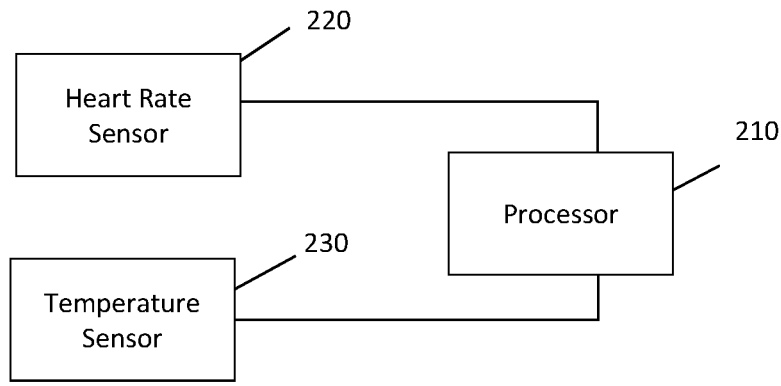
FIG. 2 illustrates a system according to at least one embodiment of the invention.

In at least one embodiment as illustrated, for example in FIG. 2, the methods discussed in connection with FIG. 1 are performed on the processor 210 running code that enables the performance of at least one method embodiment and is in communication with the heart rate sensor 220 and the temperature sensor 230. Examples of a heart rate sensor 220 include a heart rate monitor attached to the individual, a processor for receiving EKG signals from electrodes attached to the person, a processor for receiving a photoplethysmogram signal (e.g., a pulse oximeter), or a processor for receiving a ballistic-cardiogram signal. The processor used as part of the heart rate sensor 220 in at least one embodiment is the processor 210. Examples of a temperature sensor 230 configured to detect a temperature on the exterior of the individual being monitored, such as an expanse of skin, can include various analog and digital temperature sensors, and infrared thermometers. In at least one embodiment, there is a memory, data storage, or storage (not illustrated) in communication with the processor 210.

Figure 3:
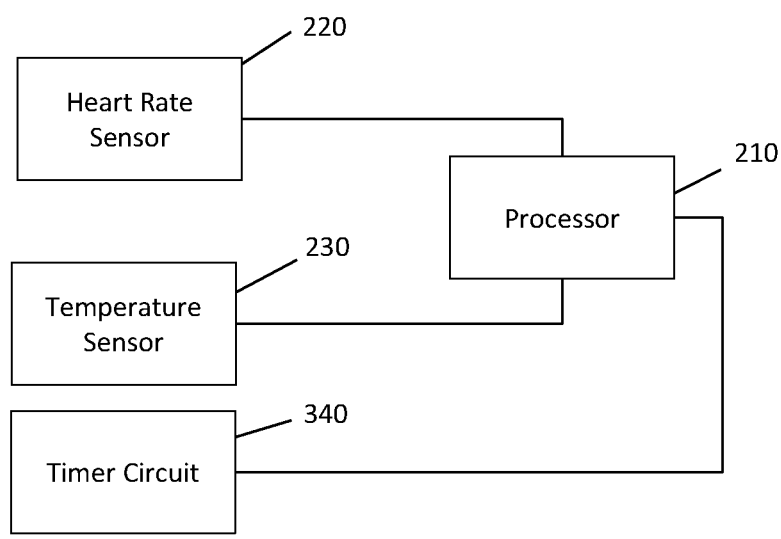
FIG. 3 illustrates a system according to at least one embodiment of the invention.

In at least one embodiment of the previous embodiments, for example as illustrated in FIG. 3, there is an optional component of the timer circuit 340 for setting or scheduling the sampling times (or intervals) at which the heart rate is used to calculate the body core temperature. In an alternative embodiment, the predetermined intervals are set by a user or the individual being monitored. In a further alternative embodiment, the predetermined time period is stored in a memory or data storage, for example, on a memory chip located on the user's wrist, in a database located on a network, or is present in the code running on the processor 210. The timer circuit 340, for example, can adjust the sampling intervals for various periods such as 30 second, 1 minute, and 5 minute intervals. The timer circuit 340 can transmit a signal to the processor 210 notifying the processor 210 to perform at least one instruction, such as alerting the processor 210 that a time interval of one minute has occurred. The timer circuit 340 can be an integrated circuit, chip, or microchip used for timing, pulse, and/or oscillator applications.

In at least one further embodiment to any of the embodiments as illustrated in FIG. 4, the system includes the alarm 450 or another similar component to produce an alert indicating the person being monitored has exceeded an alarm parameter threshold for the aPSI score as calculated by the processor 210. The alarm 450 can be contained within the system or in communication with the system to produce an alert. The alert can be produced in any sensory form, such as auditory output through a speaker, visual output through a display and/or light elements, and/or a vibration from a transducer, configured to alert the individual or a monitoring system that the PSI parameter threshold has been exceeded.

As illustrated in FIG. 5, in at least one further embodiment to any of the above embodiments, the system includes a timer circuit 340 and at least one accelerometer 555 in communication with the processor 210. The accelerometer 555 is configured to provide a signal to the processor 210 based on the individual's movements that are detected.

In a further embodiment to the above embodiments, the system includes a sensor internal to the individual being monitored to measure body core temperature. The sensor is in communication with the processor wirelessly. An example of the internal temperature sensor is a thermometer pill (Jonah™ Pill, Respironics, Inc., Bend, Oregon) that would be orally ingested.

In at least one embodiment, the processor 210, the heart rate sensor 220, the temperature sensor 230, and/or the other described electronics, such as the timer 340, the alarm 450, or the accelerometer 555, embodied in the block diagrams of FIGS. 2-5, are housed within or attached to an apparatus worn by an individual being monitored, such as on the individual's chest, arm, or wrist, but is not limited in this regard.

Figure 6:
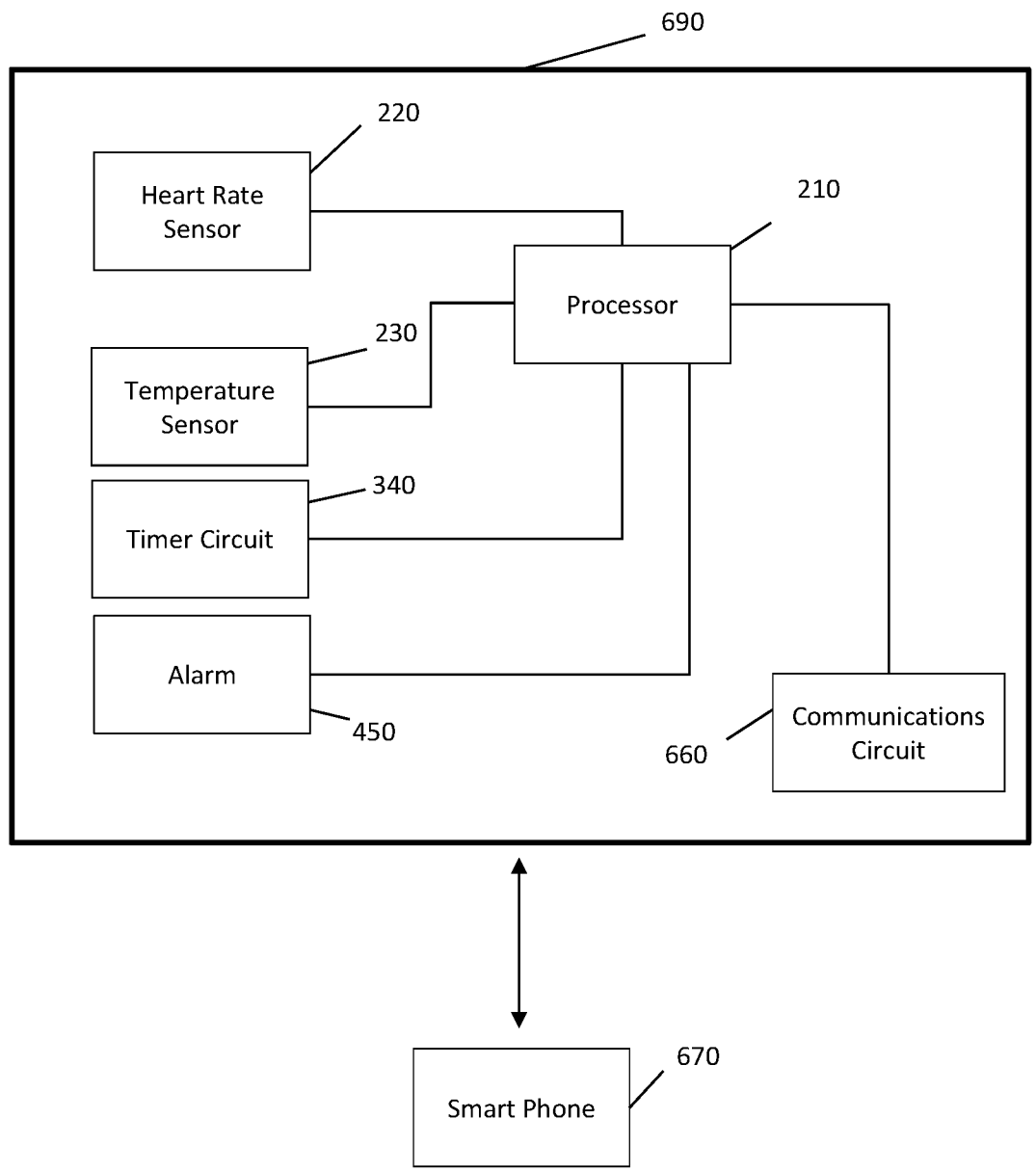
FIG. 6 illustrates a system according to at least one embodiment of the invention.

In a further embodiment illustrated in FIG. 6, the processor 210, the timer circuit 340, the alarm 450, and the accelerometer 555 are present in one housing 690, such as that provided by a smartphone or smartwatch, in wireless communication with the heart rate sensor 220 and/or the temperature sensor 230. In a further embodiment or in addition to the previous embodiments, the body core temperature, the heart rate, and/or the aPSI score can be shown on a display present on the wearable device, such as a wrist worn display, a smart telephone, or a heads up display, for viewing by the person being monitored.

In at least one embodiment, the processor 210 is detached from the individual being monitored and is located in external equipment such as a medical monitor or a computer implemented device running software according to at least one method embodiment. In such an embodiment, examples of how the information is sent to such external equipment include, but is not limited to, transmitting can be sent wirelessly including optically, or by various types or arrangements of hardwire connections, or combinations thereof. An example of wireless and optical transmissions is through a transmitter and a receiver. In a further embodiment to any of the previous embodiments, the information can be received through, for example, a user interface, such as a keyboard, graphical user interface (e.g., touchscreen) on a display, or a microphone.

The information and operations that are transmitted throughout the various described embodiments can be in the form of electronic data, wireless signals, or a variation thereof, for example. In at least one embodiment, the processor 210 can be designed to accomplish signal processing in the configured apparatus containing the sensors and electronics but can transmit signals to a network for further processing. In another embodiment, the processor 210 is connected to a communications circuit 660 to transmit the body core temperature, the skin temperature, the heart rate, and/or the aPSI score to an external system for monitoring and/or display. FIG. 6 illustrates a communications circuit 660 configured to communicate directly with the external system, such as the communications circuit 660 communicating directly with a smart phone 670. The information and operations that are transmitted throughout the various embodiments can be sent wirelessly, optically, or by various types or arrangements of hard wire connections, or combinations thereof, among the various system components, for example.

In a further embodiment, the system includes one or more means instead of a particular component.

A heart rate means for detecting a heart rate includes a sensor for measuring heart beats or blood flow, a heart rate sensor, a heart monitor, or another biotelemetry device configured to detect a heartbeat, heart rate, or blood flow but is not limited in this regard and the means for measuring a heart rate or heart beat can be measured in real time or recorded for later use.

In at least one embodiment, a temperature means for measuring the skin temperature can include various manual or digital thermometer and temperature gauges, but is not limited in this regard and additional apparatuses configured to detect heat or temperature can be used. The temperature means can detect skin temperature of an area of a body, such as an area of skin, can include a manual or digital thermometer, a temperature gauge, for example but is not limited in this regard and additional apparatuses configured to detect heat or temperature of an area of a body can be used.

An input means for receiving input, such as receiving a user's age includes a user interface such as a keyboard, graphical user interface (e.g., touchscreen) on a display, or voice recognition interface but is not limited in this regard and can also include receiving data from a device, memory, database, data storage, or apparatus configured to store or transmit data.

In at least one embodiment, a calculation means for calculating an aPSI score for the person based on the detected skin temperature, the detected heart rate, the received input age, and temperature gradient between the detected skin temperature and a body core temperature calculated based on the detected heart rate is the processor with suitable programming to perform the steps associated with this function.

In an alternative embodiment, the Kalman filter model or the extended Kalman filter model is adjusted for fitness level. In particular, the aPSI score can be adjusted by increasing it for better fitness and decreasing it for lower fitness levels. In a further alternative embodiment, the Kalman filter is adjusted based on age of the person by adjusting the maximum heart rate used in the model to reflect the person's age. An example of one way to determine maximum heart rate is to use 220 minus the person's age; however, the maximum heart rate could be determined for the person based on physiological testing prior to use of the heart rate sensor. In at least one embodiment, the maximum heart rate is adjusted to reflect the heart rate for the person while leaving the starting heart rate alone and thereby adjusting the scale of the correlation between the heart rate and the body core temperature. In a further alternative embodiment, any combination of the fitness, age, resting heart rate, and maximum heart rate are used to adapt or fine-tune the aPSI score the monitored individual.

As will be appreciated by one skilled in the art based on this disclosure, aspects of the present invention may be embodied as a system, method or computer program product. Accordingly, aspects of the present invention may take the form of an entirely hardware embodiment, a processor operating with software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this disclosure, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Computer program code for carrying out operations for aspects of the present invention may be written in any combination of one or more programming languages, including an object oriented programming language such as Xcode® (Apple Inc.), Ruby, Python™ (Python Software Foundation), Java® (Oracle America Inc.), Smalltalk, Objective C, C++, C#, Microsoft® Transact-SQL, XML, or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including Bluetooth®, which is a registered certification mark of Bluetooth SIG, Inc., communication protocol; a local area network (LAN) or a wide area network (WAN); or the connection may be made to an external computer (for example, through the Internet using an Internet Service Provider).

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute with the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 7:
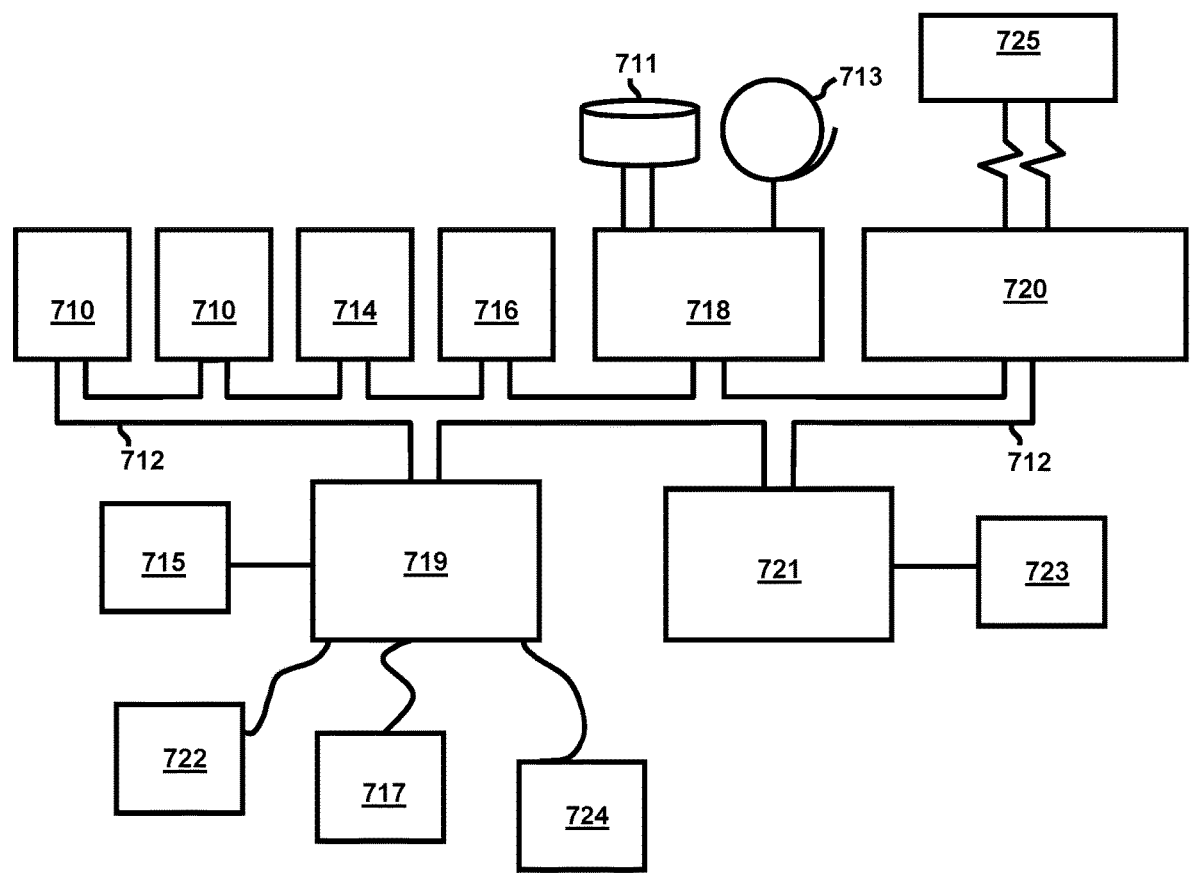
FIG. 7 illustrates a computer program product and computer implementation according to at least one embodiment of the invention.

Referring now to FIG. 7, a representative hardware environment for practicing at least one embodiment of the invention is depicted. This schematic drawing illustrates a hardware configuration of an information handling/computer system in accordance with at least one embodiment of the invention. The system comprises at least one processor or central processing unit(s) (CPU) 710. The CPU(s) 710 are interconnected with system bus 712 to various devices such as a random access memory (RAM) 714, read-only memory (ROM) 716, and an input/output (I/O) adapter 718. The I/O adapter 718 can connect to peripheral devices, such as disk units 711 and tape drives 713, or other program storage devices that are readable by the system. The system can read the inventive instructions on the program storage devices and follow these instructions to execute the methodology of at least one embodiment of the invention. The system further includes a user interface adapter 719 that connects a keyboard 715, mouse 717, speaker 724, and/or other user interface devices such as a touch screen device 722 to the bus 712 to gather user input. Additionally, a communication adapter 720 connects the bus 712 to a data processing network 725, and a display adapter 721 connects the bus 712 to a display device 723 which may be embodied as an output device such as a monitor, printer, or transmitter, for example.

The flowchart and block diagrams in the Figures illustrate the architecture, functionality, and operation of possible implementations of systems, methods and computer program products according to various embodiments of the present invention. In this regard, each block in the flowchart or block diagrams may represent a module, circuit, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the root terms "include" and/or "have", when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means plus function elements in the claims below are intended to include any structure, or material, for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention.

Although the present invention has been described in terms of particular example embodiments, it is not limited to those embodiments. The embodiments, examples, and modifications which would still be encompassed by the invention may be made by those skilled in the art, particularly in light of the foregoing teachings.

As used above "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

Those skilled in the art will appreciate that various adaptations and modifications of the embodiments described above can be configured without departing from the scope and spirit of the invention. Therefore, it is to be understood that, within the scope of the appended claims, the invention may be practiced other than as specifically described herein.

VI. INDUSTRIAL APPLICABILITY

The disclosed embodiments provide an improved way to detect HRIs based upon an individual's a PSI taking into account an impact of the clothing worn by the individual. In some embodiments, the systems and methods provide a mechanism to alert the individual of the potential for HRI based on their aPSI.

The invention claimed is:

1. A system for generating an adaptive physiological strain index (aPSI) to reduce a likelihood of heat related illness (HRI) or treat for HRI of an individual based on the aPSI, the system comprising:
at least one heart rate sensor configured to measure a heart rate of the individual;
at least one temperature sensor configured to detect a skin temperature of the individual;
a processor in electrical communication with said at least one temperature sensor and said at least one heart rate sensor, said processor configured to produce the aPSI for the individual using the heart rate from said at least one heart rate sensor and an adaptive maximum body temperature based in part on a temperature gradient between the skin temperature and a body core temperature; and a monitoring system in communication with said processor, said monitoring system configured to provide an alert identifying a treatment based on the aPSI to the individual or another individual when the aPSI is above a predetermined aPSI threshold for the individual, and wherein the aPSI and the alert are used by the individual or the other individual to begin the treatment selected from having the individual adjust a level of activity or pace of the individual to lower the aPSI, drink fluids, submerse in water, and/or sit in a cooler environment to address physical strain;

wherein the at least one treatment identified by the alert updates as the aPSI for the individual changes; and wherein when the aPSI is below the predetermined aPSI threshold, said system continues to monitor the individual.

2. The system of claim 1, further comprising a housing containing said at least one heart rate sensor and said at least one temperature sensor, and wherein said monitoring system includes a display configured to provide the alert as a visual alert.

3. The system of claim 1, further comprising a memory in electrical communication with said processor, and wherein said processor calculating the aPSI for the individual uses only
the heart rate from said at least one heart rate sensor,
the adaptive maximum body temperature based on
the temperature gradient between the skin temperature from said at least one temperature sensor and the body core temperature, the temperature gradient varies over time, and
a critical temperature,
the skin temperature from said at least one skin temperature sensor,
a resting body core temperature from said memory,
a resting heart rate from said memory,
a current heart rate from said at least one heart rate sensor, and the body core temperature from an internal temperature sensor or calculated from the current heart rate, and
a critical heart rate.

4. The system of claim 1, further comprising a data storage configured to store a body core temperature at rest and a heart rate at rest; and wherein said processor calculating the aPSI based on the following equation:

$$aPSI = 5\left(\frac{CT_t - CT_{rest}}{CT_{critical} - CT_{rest}}\right) + 5\left(\frac{HR_t - HR_{rest}}{HR_{critical} - HR_{rest}}\right)$$

$$CT_{critical} = 39.5° \text{ C.} + \frac{(CT_t - ST_t) - 4}{4}$$

where $CT_t$ is the body core temperature at a time t, $CT_{rest}$ is the body core temperature at rest, $HR_t$ is the heart rate at a time t, $HR_{rest}$ is the heart rate at rest, $HR_{critical}$ is a maximum heart rate, $CT_{critical}$ is the adaptive maximum body temperature, and ST is the skin temperature.

5. The system according to claim 1, further comprising a timer circuit in communication with said processor, and wherein said processor is configured to produce a new calculated aPSI based on calculating at least one first aPSI at an initial time designation of a timer circuit and calculating one new calculated aPSI at each predetermined time interval as provided by said timer circuit.

6. The system according to claim 1, further comprising an accelerometer in communication with said processor; and wherein said processor is configured to detect at least one of a resting heart rate and a resting skin temperature of the individual when a plurality of signals from said accelerometer remain below a predetermined threshold for a predetermined time period and/or substantially remain below the predetermined threshold for the predetermined time period, and said processor is further configured to determine a resting body core temperature for the individual based on the resting heart rate.

7. The system according to claim 1, wherein said processor is configured to calculate the body core temperature using a Kalman filter or an extended Kalman filter.

8. The system according to claim 1, further comprising a display in communication with said processor to display the aPSI produced by the processor.

9. The system according to claim 1, further comprising an alarm in communication with said processor, wherein said processor is configured to produce an alert signal to said alarm when the aPSI exceeds the predetermined aPSI threshold.

10. The system according to claim 1, further comprising:
a memory for storing at least a resting heart rate for the individual, and said memory is in electrical communication with said processor;
wherein said processor configured to produce an updated aPSI for the individual based on a current skin temperature, the resting heart rate, and a current heart rate where a current body core temperature is calculated based on the heart rate information and time since initiation of a monitoring session of the individual.

11. The system according to claim 1, further comprising:
at least one internal temperature sensor configured to be internal to the individual to provide the body core temperature;
wherein said processor configured to produce an updated aPSI for the individual based on the skin temperature from said at least one skin temperature sensor, a resting heart rate from a memory, a current heart rate from said at least one heart rate sensor, and the body core temperature from said internal temperature sensor.

12. A method for generating an adaptive physiological strain index (aPSI) from at least one body core temperature and at least one heart rate for an individual to reduce a likelihood of heat related illness (HRI) or treat for HRI of an individual based on the aPSI, the method comprising:
receiving by a processor a heart rate signal or the heart rate from a heart rate sensor worn by the individual;
receiving by the processor a skin temperature reading from a temperature sensor detecting a skin temperature of the individual;
receiving, estimating, or calculating with the processor the body core temperature for the individual;
calculating with the processor an adaptive maximum body temperature based on a temperature gradient between the skin temperature reading and the body core temperature;
calculating with the processor the aPSI for the individual using the body core temperature, the adaptive maximum body temperature, and the heart rate signal or the heart rate; and
producing the aPSI from the processor;
repeating the method at predetermined intervals to calculate updated aPSI scores for the individual; and if the aPSI is above a threshold, then
alerting the individual by identifying a treatment selected based on the aPSI from a group consisting of adjusting a level of activity or pace of the individual to lower the aPSI, drinking fluids, submersing in water, and/or sitting in a cooler environment to address physical strain preventing or treating the individual for HRI, and
continuing the method allowing the individual to monitor how effective the lowering of the aPSI is; and
if the aPSI is below the threshold, the method continues.

13. The method of claim 12, wherein producing the aPSI includes sending the aPSI to an external device,
the method further comprising displaying a visual indicator of the received aPSI for the individual on the external device.

14. The method of claim 12, further comprising
determining the heart rate from the heart rate signal; and
sending with a communications circuit the skin temperature and the heart rate to the processor located on an external system from the heart rate sensor and the temperature sensor.

15. The method of claim 12, wherein calculating the aPSI for the individual uses only
the heart rate from said at least one heart rate sensor,
the adaptive maximum body temperature based on
the temperature gradient between the skin temperature from said at least one temperature sensor and the body core temperature, the temperature gradient varies over time, and
a critical temperature,
a current skin temperature from said at least one skin temperature sensor,
a resting body core temperature from a memory,
a resting heart rate from said memory,
a current heart rate from said at least one heart rate sensor, and the body core temperature from an internal temperature sensor, and
a critical heart rate.

16. The method of claim 12, wherein calculating the aPSI is based on said processor calculating the aPSI based on the following equation:

$$aPSI = 5\left(\frac{CT_t - CT_{rest}}{CT_{critical} - CT_{rest}}\right) + 5\left(\frac{HR_t - HR_{rest}}{HR_{critical} - HR_{rest}}\right)$$

$$CT_{critical} = 39.5° \text{C.} + \frac{(CT_t - ST_t) - 4}{4}$$

where $CT_t$ is the body core temperature at a time t, $CT_{rest}$ is the body core temperature at rest, $HR_t$ is the heart rate at a time t, $HR_{rest}$ is the heart rate at rest, $HR_{critical}$ IS a maximum heart rate, and $CT_{critical}$ is the adaptive maximum body temperature.

17. The method of claim 12, wherein calculating with the processor the body core temperature uses a Kalman filter or an extended Kalman filter.

18. The method according to claim 12, wherein for generating the aPSI from the skin temperature, the body core temperature and the heart rate, the method comprising:
when one of the skin temperature and the heart rate from the heart rate signal is unavailable, using a previously stored value or calculating a value for the unavailable skin temperature or the unavailable heart rate.

19. The method according to claim 12, wherein calculating the aPSI for the individual is based on the skin temperature reading received from the temperature sensor, a resting heart rate, the heart rate signal received from the heart rate sensor, and the body core temperature calculated based on the heart rate signal.

20. A system for generating an adaptive physiological strain index (aPSI) to reduce a likelihood of heat related illness (HRI) or treat for HRI of an individual based on the aPSI, the system comprising:
at least one heart rate sensor configured to be worn by an individual;
at least one temperature sensor configured to detect a skin temperature of the individual;
a memory for storing at least a resting heart rate and a resting body core temperature for the individual; and
a processor in electrical communication with said at least one temperature sensor, said at least one heart rate sensor, and said memory, said processor configured to produce the aPSI for the individual using only
a heart rate from said at least one heart rate sensor,
an adaptive maximum body temperature based on
a temperature gradient between the skin temperature from said at least one temperature sensor and a body core temperature, the temperature gradient varies over time, and
a critical temperature,
a current skin temperature from said at least one skin temperature sensor,
a resting body core temperature from said memory,
a resting heart rate from said memory,
a current heart rate from said at least one heart rate sensor, and the body core temperature from an internal temperature sensor, and
a critical heart rate; and
a monitoring system in communication with said processor, said monitoring system includes a display configured to provide a visual alert to the individual or another individual of the aPSI for the individual, and
wherein the aPSI is used to select a treatment to be included in the alert, the treatment is selected from a group including having the individual adjust a level of activity or pace of the individual to lower the aPSI, drink fluids, submerse in water, and/or sit in a cooler environment to address physical strain when the aPSI is above a predetermined aPSI threshold to prevent or treat the individual for HRI, said system continues to monitor the individual and allows the individual or other individual to monitor an effectiveness of the treatment; and
when the aPSI is below the predetermined aPSI threshold, said system continues to monitor the individual.

* * * * *